(12) United States Patent
Rangwala et al.

(10) Patent No.: US 11,827,862 B2
(45) Date of Patent: Nov. 28, 2023

(54) DURABLE SURFACE COATINGS

(71) Applicant: MicroVention, Inc., Aliso Viejo, CA (US)

(72) Inventors: Hussain Rangwala, Villa Park, CA (US); William R. Patterson, Huntington Beach, CA (US); Aaron Baldwin, Orange, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 0 days.

(21) Appl. No.: 17/396,471

(22) Filed: Aug. 6, 2021

(65) Prior Publication Data

US 2022/0041950 A1  Feb. 10, 2022

Related U.S. Application Data

(60) Provisional application No. 63/062,995, filed on Aug. 7, 2020.

(51) Int. Cl.

| | | |
|---|---|---|
| C10M 111/04 | (2006.01) | |
| C10M 105/76 | (2006.01) | |
| C10M 107/42 | (2006.01) | |
| C10M 177/00 | (2006.01) | |
| C10N 70/00 | (2006.01) | |
| C10N 50/00 | (2006.01) | |
| C10N 40/00 | (2006.01) | |

(52) U.S. Cl.
CPC ......... *C10M 111/04* (2013.01); *C10M 105/76* (2013.01); *C10M 107/42* (2013.01); *C10M 177/00* (2013.01); *C10M 2217/0245* (2013.01); *C10M 2227/045* (2013.01); *C10N 2040/50* (2020.05); *C10N 2050/023* (2020.05); *C10N 2070/00* (2013.01)

(58) Field of Classification Search
CPC .............. C10M 177/00; C10M 105/76; C10M 107/42; C10M 111/04; C10M 2217/0245; C10M 2227/045; C10N 2040/50; C10N 2050/023; C10N 2070/00; A61L 29/085; A61L 31/14; A61L 31/022; A61L 31/10; A61L 29/14; A61L 29/02; A61L 2420/08; A61L 2420/02
See application file for complete search history.

(56) References Cited

U.S. PATENT DOCUMENTS

| | | | | |
|---|---|---|---|---|
| 5,736,251 A | * | 4/1998 | Pinchuk | A61L 31/10 606/1 |
| 6,706,408 B2 | * | 3/2004 | Jelle | A61L 29/085 427/457 |
| 2006/0251795 A1 | * | 11/2006 | Kobrin | A61L 27/34 427/535 |
| 2013/0261566 A1 | * | 10/2013 | Lockwood | A61L 29/14 523/105 |

\* cited by examiner

*Primary Examiner* — Vishal V Vasisth
(74) *Attorney, Agent, or Firm* — K&L Gates LLP; Brian J. Novak; Benjamin D. Heuberger

(57) ABSTRACT

Described herein are durable coatings, i.e. for medical devices, and methods of forming the coatings.

22 Claims, 1 Drawing Sheet

DURABLE SURFACE COATINGS

RELATED APPLICATIONS

This application claims priority of U.S. Provisional Patent Application No. 63/062,995, filed Aug. 7, 2020, the entire content of which is incorporated by reference.

FIELD

Described herein are durable surface coatings, which are useful for medical devices, and processes for preparing the coatings.

BACKGROUND

Hydrophilic coatings used on medical devices, including guidewires and catheters, are generally on the order of microns thick. Upon hydration and repetitive use such coatings have been known to shed particulates by, for example, separating from the access device surface during interventional procedures. Most coatings are mechanically adhered to a surface. Forces exerted during insertion and navigation of an access device can shear the coatings and release particulate matter that may cause various medical complications depending on the particulate size, including blood vessel ischemia.

Thus, there remains a need for improved surface coatings that are useful for, at least, medical devices.

SUMMARY

Described herein are surface coatings. In some embodiments the surface coatings provide improved durability, i.e. a reduced propensity to shed coating particulate upon hydration of the coating or repetitive use of a device on which the coating is disposed. In some embodiments, the surface coatings can be disposed on a substrate, which can be associated with a medical device such as a catheter, a guide wire, or an implantable medical device such as a stent. Implantable medical devices can include, but are not limited to, flat coupons, hypo tubes, wires, woven wires, or laser cut objects. In some embodiments, the medical device is one used to access a lumen of a subject's body.

DETAILED DESCRIPTION

Figure 1:
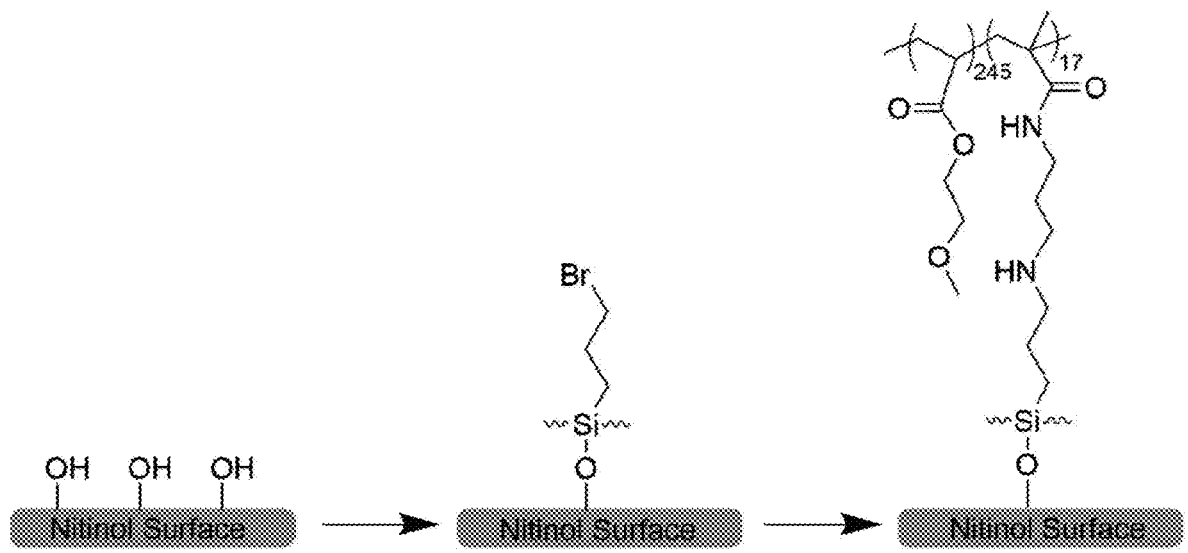
FIG. 1 shows an example of a coating, and a general process for preparing the coating on a surface.

Described herein are substrate coatings, i.e. durable surface coatings, and processes for preparing the coatings. In some embodiments, the coatings can be used for medical devices.

Definitions

Listed below are definitions of various terms used to describe the compositions and methods provided herein. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which the compositions and methods provided herein pertain. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e. to at least one) of the grammatical object of the article. By way of example, "an element" means one element or more than one element. Furthermore, use of the term "including" as well as other forms, such as "include", "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed compositions and methods.

Coatings

Surface coatings are described. Thus, in one aspect described are coatings, comprising a base coat and a top coat covalently linked to the base coat, wherein the base coat includes an alkylsilanyl moiety, and the top coat includes a hydrophilic or amphiphilic polymeric moiety having an amine moiety.

In some embodiments, the coating is covalently linked to a surface. Thus, provided herein are surfaces, comprising the coatings described herein covalently linked to the surfaces. In some embodiments, the surface is a surface of a medical device. In some embodiments, the medical device is a catheter, a guide wire, a stent, or an access device. Thus, in some embodiments described are medical devices having a portion of its surface, or all of its surfaces, coated with the one or more of the coatings provided herein. In some embodiments, a medical device is described, comprising a coating described herein covalently linked to a surface of the medical device.

In some embodiments, the polymeric moiety is a p(MEA-co-APMA) polymer, an amine functionalized poly(ethylene glycol) polymer, an amine functionalized poly(vinyl alcohol), an amine functionalized hyaluronic acid, an amine functionalized poly(vinyl pyrrolidone), or a combination thereof.

In some embodiments, the alkylsilanyl moiety is ($C_{1-20}$ alkyl)silanyl.

In some embodiments, the alkylsilanyl moiety is propylsilanyl, propylmethoxysilanyl, propyldimethoxysilanyl, heptylsilanyl, heptylmethoxysilanyl, heptyldimethoxysilanyl, undecylsilanyl, undecylmethoxysilanyl, undecyldimethoxysilanyl, or a combination thereof.

In some embodiments, the base coat and top coat are covalently linked such that an aminoalkylsilanyl moiety is present.

In some embodiments, the amine moiety is a secondary amine or a tertiary amine.

In some embodiments, the coating is about 100 nanometers thick or less. In some embodiments, the coating is about 10 nanometers thick or less. In some embodiments, the coating is about 1 nanometer thick.

In some embodiments, the coatings include a structure according to Formula I:

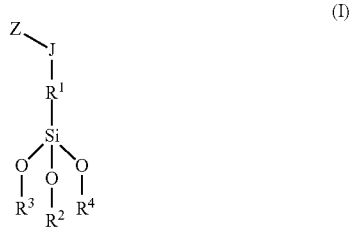
(I)

wherein
Z-J is the polymeric moiety described above, and J is the amine of the polymeric moiety;
$R^1$ is $C_{1-20}$ alkyl;
$R^2$ is a substrate;
$R^3$ and $R^4$ are each, independently, $C_{1-6}$ alkyl, or each of $R^3$ and $R^4$ may be a bond that is covalently linked to $R^2$.

In some embodiments, the coatings include a structure according to Formula II:

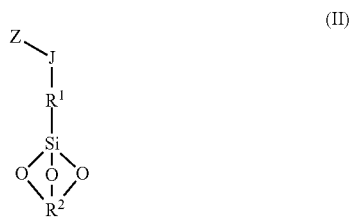
(II)

wherein Z-J, $R^1$, and $R^2$ are as defined above.

In some embodiments, the coatings include a structure according to Formula III:

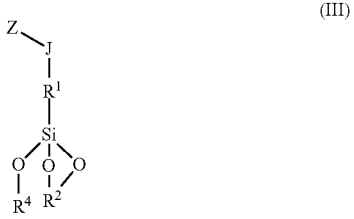
(III)

wherein Z-J, $R^1$, and $R^2$ are as defined above, and $R^4$ is $C_{1-6}$ alkyl.

In some embodiments, the coatings include a structure according to Formula IV:

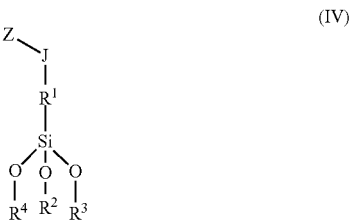
(IV)

wherein Z-J, $R^1$, and $R^2$ are as defined above, and $R^3$ and $R^4$ are each, independently, $C_{1-6}$ alkyl.

In some embodiments, J is a secondary amine. In some embodiments, J is a tertiary amine. In some embodiments, the coatings provided herein include more than one structure of the Formulae provided such that the coatings include J being a secondary amine on one of the Formulae, and J being a tertiary amine on another of the Formulae.

In some embodiments, the coating includes a combination of the structures selected from Formula II, Formula III, or Formula IV.

A substrate's material composition can be, for example, any metallic/alloy (including, but not limited to, nitinol, stainless steel, cobalt chromium), any plastic/polymer (including, but not limited to, grilamide, Pbax, PEEK), any glass surfaces, any surface including hydroxyl moieties on the surface, or any surface that can be treated to provide hydroxyl moieties on the surface.

The substrates can be virtually in any form. In some embodiments, the substrate is an access device. In some embodiments, the substrate is a catheter. In some embodiments, the substrate is a guide wire. In some embodiments, the substrate is formed into an implantable medical device. In some embodiments, the substrate may be in the form of a flat coupon, hypo tube, wire, woven wire, or laser cut object. In some embodiments, the substrate may be formed into a stent such as a braided stent platform.

One advantage of the coatings provided herein is that they can provide a surface (i.e. of a medical device) having a coating with enhanced durability, enhanced lubricity, or enhanced durability and lubricity.

Coating Processes

In one embodiment, surface modification of a substrate surface is described. In one embodiment, the substrate surface is a hydroxylated substrate surface.

One method of surface functionalizing a substrate is through silane chemistry. Haloalkylsilanes represent one possible compound having reactivity suitable for substrate modification. FIG. 1 indicates one suggested pathway that haloalkylsilanes may react with a hydroxylated substrate surface. The covalent linkage of haloalkylsilanes to a hydroxylated substrate can yield linkages having one, two, or three covalent bonds between the haloalkylsilane and the substrate surface. Herein, haloalkysilanes are used as a base coat of the substrate surface to further react biocompatible molecules or polymers as a top coat to a substrate surface, such as a surface of a medical device.

In some embodiments, a substrate to be coated is treated with a hydroxylating agent to induce the presence of hydroxyl moieties on the surface. Such hydroxylating agents include, but are not limited to, hydrogen peroxide or plasma treatments.

Once a hydroxylated surface is obtained, a halo-silane (in some embodiments a haloalkylsilane) can be used to activate the surface for amine functional polymer bonding.

In some embodiments, the haloalkylsilane has a structure according to Formula V:

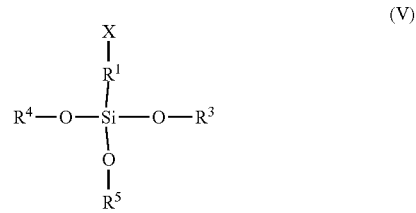
(V)

wherein
X is iodo, chloro, or bromo;
$R^1$ is $C_{1-20}$ alkyl; and
each of $R^3$, $R^4$, and $R^5$ are, independently, $C_{1-6}$ alkyl.

In some embodiments, the haloalkylsilane has a structure according to Formula VI:

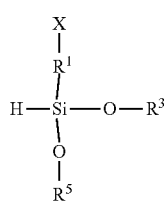
(VI)

wherein
X is iodo, chloro, or bromo;
$R^1$ is $C_{1-20}$ alkyl; and
each of $R^3$ and $R^5$ are, independently, $C_{1-6}$ alkyl.

In some embodiments, the haloalkylsilane has a structure according to Formula VII:

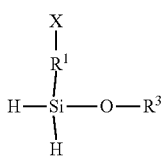
(VII)

wherein
X is iodo, chloro, or bromo;
$R^1$ is $C_{1-20}$ alkyl; and
$R^3$ is $C_{1-6}$ alkyl.

In some embodiments of these Formulae, X is bromo.
In some embodiments of the Formulae provided herein, $R^1$ is $C_{3-11}$ alkyl.
In some embodiments of the Formulae provided herein, each of $R^3$, $R^4$, and $R^5$ are, independently, methyl or ethyl.
In some embodiments, each of $R^3$, $R^4$, and $R^5$ are methyl.
In some embodiments, X is bromo, and $R^3$ is methyl.
In some embodiments, the haloalkylsilane is halopropylsilanyl, halopropylmethoxysilanyl, halopropyldimethoxysilanyl, haloheptylsilanyl, haloheptylmethoxysilanyl, haloheptyldimethoxysilanyl, haloundecylsilanyl, haloundecylmethoxysilanyl, haloundecyldimethoxysilanyl, or a combination thereof.
In some embodiments, halo is iodo, choro, or bromo. In some embodiments, halo is bromo.
In some embodiments, described herein are processes for forming the coatings described herein, including contacting a haloalkylsilanyl moiety with a polymeric moiety having an amine moiety to form the coating.
In some embodiments, the polymeric moiety is a hydrophilic polymeric moiety. In some embodiments, the polymeric moiety is an amphiphilic polymeric moiety.
In some embodiments, the haloalkylsilanyl moiety is halopropylsilanyl, halopropylmethoxysilanyl, halopropyldimethoxysilanyl, haloheptylsilanyl, haloheptylmethoxysilanyl, haloheptyldimethoxysilanyl, haloundecylsilanyl, haloundecylmethoxysilanyl, haloundecyldimethoxysilanyl, or a combination thereof. In some embodiments, the halo is iodo, chloro, or bromo. In some embodiments, the halo is bromo.

In some embodiments, described herein are processes for coating a medical device, including:
a) contacting a halosilanyl compound with a surface of the medical device to form a base coat; and
b) contacting the base coat with a hydrophilic polymeric moiety having an amine moiety to form a top coat,
wherein the base coat is covalently linked to the surface of the medical device, and the top coat is covalently linked to the base coat.

In some embodiments of the processes described herein, the halosilanyl compound is 3-bromopropyltrimethoxysilane, 7-bromoheptyltrimethoxysilane, 11-bromoundecyltrimethoxysilane, or a combination thereof.

In some embodiments, the process is performed with the surface of the medical device at least partially submerged in a solution.

In some embodiments, the processes further comprise a curing step subsequent to forming the base coat and prior to forming the top coat.

In some embodiments, the processes further comprise contacting the surface of the medical device with a hydroxylating agent prior to forming the base coat.

One advantage of the processes provided herein is that a single layer of base coat and top coat can be disposed on the surface, thereby providing a single coating layer on the surface that is on the order of one nanometer thick. By contrast, multiple layers are bonded in traditional guidewire and catheter coating technologies that produce micron thick coatings.

EXAMPLES

The following Examples further illustrate aspects of the compositions and methods provided herein. However, these Examples are in no way a limitation of the teachings or disclosure as set forth herein. These Examples are provided for illustration purposes.

Example 1: Applying a Coating to a Surface

A coating was applied to electropolished nitinol wires as shown in FIG. 1. The metallic substrate was hydroxylated, covalently functionalized with a bromo-silane, then an amine-functionalized polymer [p(MEA-co-APMA)] (N-(3-aminopropyl)methacrylamide=APMA, and 2-methoxyethyl acrylate=MEA) was covalently attached.

Example 2: Lubricity Assessment

Figure 2:
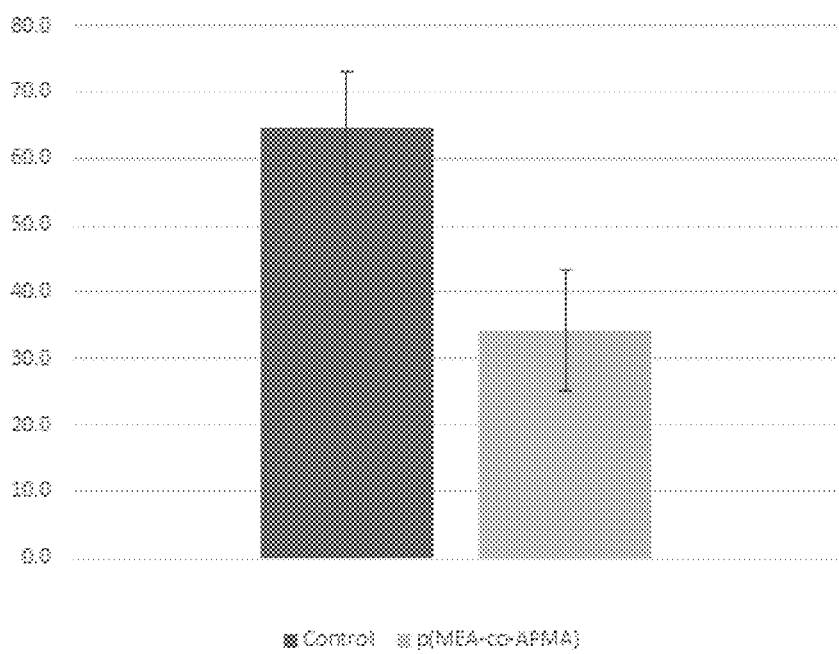
FIG. 2 shows the average tensile pull force (g) with 900 g Teflon clamp force of a coated nitinol wire compared to a control, as described in Example 1.

The coated nitinol wires prepared in Example 1 were tested using an OakRiver durability and lubricity test system. Tests were performed by pulling the coated nitinol wire through Teflon pad grips set at a clamping force of 900 g. Initial data, shown in FIG. 2, indicated the average pull friction was reduced by 47% relative to control.

INCORPORATION BY REFERENCE AND EQUIVALENTS

The contents of all references (including literature references, issued patents, published patent applications, and co-pending patent applications) cited throughout this application are hereby expressly incorporated herein by reference in their entireties. Unless otherwise defined, all technical and scientific terms used herein are accorded the meaning commonly known to one of ordinary skill in the art.

Those skilled in the art will recognize, or be able to ascertain using no more than routine experimentation, numerous equivalents to the specific procedures, embodiments, claims, and examples described herein. Such equivalents are intended to be encompassed by the following claims.

It is to be understood that wherever values and ranges are provided herein, all values and ranges encompassed by these values and ranges, or a combination of these values and ranges, are meant to be encompassed within the scope of the aspects and embodiments provided herein. Moreover, all values that fall within these ranges, as well as the upper or lower limits of a range of values, are also contemplated by the present application.

What is claimed is:

1. A coating, comprising a base coat and a top coat covalently linked to the base coat, wherein the base coat includes an alkylsilanyl moiety, and the top coat includes a polymeric moiety having an amine moiety, wherein the coating is about 100 nanometers thick or less.

2. The coating of claim 1, wherein the coating is covalently linked to a surface.

3. The coating of claim 1, wherein the polymeric moiety is a poly(MEA-co-APMA) polymer, an amine functionalized poly(ethylene glycol) polymer, an amine functionalized poly(vinyl alcohol), an amine functionalized hyaluronic acid, or a combination thereof.

4. The coating of claim 1, wherein the alkylsilanyl moiety is ($C_{1-20}$ alkyl)silanyl.

5. The coating of claim 1, wherein the alkylsilanyl moiety is propylsilanyl, propylmethoxysilanyl, propyldimethoxysilanyl, heptylsilanyl, heptylmethoxysilanyl, heptyldimethoxysilanyl, undecylsilanyl, undecylmethoxysilanyl, undecyldimethoxysilanyl, or a combination thereof.

6. The coating of claim 1, wherein the base coat and top coat are covalently linked such that an aminoalkylsilanyl moiety is present.

7. The coating of claim 1, wherein the amine moiety is a secondary amine or a tertiary amine.

8. The coating of claim 1, wherein the coating is about 10 nanometers thick or less.

9. The coating of claim 1, wherein the coating is about 1 nanometer thick.

10. A medical device, comprising the coating of claim 1 covalently linked to a surface of the medical device.

11. A process for forming a coating, comprising a base coat and a top coat covalently linked to the base coat, wherein the base coat includes an alkylsilanyl moiety, and the top coat includes a polymeric moiety having an amine moiety,
    wherein the coating is 100 nanometers thick or less,
    wherein the process comprises contacting the alkylsilanyl moiety with the polymeric moiety having an amine moiety to form the coating, and
    wherein the alkylsilanyl moiety is a haloalkylsilanyl moiety.

12. The process of claim 11, wherein the haloalkylsilanyl moiety is halopropylsilanyl, halopropylmethoxysilanyl, halopropyldimethoxysilanyl, haloheptylsilanyl, haloheptylmethoxysilanyl, haloheptyldimethoxysilanyl, haloundecylsilanyl, haloundecylmethoxysilanyl, haloundecyldimethoxysilanyl, or a combination thereof.

13. The process of claim 12, wherein the halo is bromo.

14. A process for coating a medical device, including:
    a) contacting a halosilanyl compound with a surface of the medical device to form a base coat; and
    b) contacting the base coat with a hydrophilic polymeric moiety having an amine moiety to form a top coat,
    wherein the base coat is covalently linked to the surface of the medical device, and the top coat is covalently linked to the base coat, and
    wherein a combined thickness of the base coat and top coat is about 100 nanometers or less.

15. The process of claim 14, wherein the halosilanyl compound is 3-bromopropyltrimethoxysilane, 7-bromoheptyltrimethoxysilane, 11-bromoundecyltrimethoxysilane, or a combination thereof.

16. The process of claim 14, wherein the process is performed with the surface of the medical device at least partially submerged in a solution.

17. The process of claim 14, further comprising a curing step subsequent to forming the base coat and prior to forming the top coat.

18. The process of claim 14, further comprising contacting the surface of the medical device with a hydroxylating agent prior to forming the base coat.

19. A surface, comprising the coating of claim 1 covalently linked to the surface.

20. The coating of claim 1, wherein the alkylsilanyl moiety is a bromo silane, and the polymeric moiety having an amine moiety is a copolymer of 2-methoxyethyl acrylate and N-(3-aminopropyl)methacrylamide.

21. The coating of claim 1, wherein the alkylsilanyl moiety is 3-bromopropyltrimethoxysilane, and the polymeric moiety having an amine moiety is a copolymer of 2-methoxyethyl acrylate and N-(3-aminopropyl)methacrylamide.

22. The coating of claim 1, comprising the structure

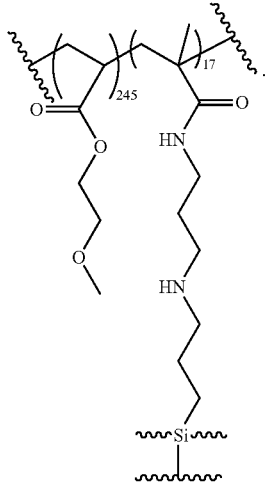

* * * * *